United States Patent
Mark et al.

[11] Patent Number: 6,120,518
[45] Date of Patent: Sep. 19, 2000

[54] NON-REFLECTIVE SURFACES FOR SURGICAL PROCEDURES

[75] Inventors: Joseph L. Mark, Indianapolis; Michael E. Miller, Trafalgar, both of Ind.

[73] Assignee: Promex, Inc., Franklin, Ind.

[21] Appl. No.: 09/053,429

[22] Filed: Apr. 1, 1998

[51] Int. Cl.$^7$ ............................................. A61B 17/32
[52] U.S. Cl. ........................................ 606/170; 606/4
[58] Field of Search .......................... 606/160, 170, 606/107, 184, 222, 4; 428/632

[56] References Cited

U.S. PATENT DOCUMENTS

| | | |
|---|---|---|
| 2,895,814 | 7/1959 | Clark . |
| 3,736,043 | 5/1973 | Sambucetti . |
| 3,756,937 | 9/1973 | Lucas et al. . |
| 3,900,374 | 8/1975 | Haggerty . |
| 4,045,312 | 8/1977 | Satoshi . |
| 4,408,215 | 10/1983 | Kitchen . |
| 4,681,665 | 7/1987 | Guillermet et al. . |
| 4,726,368 | 2/1988 | Morris ........................ 606/160 |
| 4,853,098 | 8/1989 | Drinkwine . |
| 5,047,008 | 9/1991 | De Juan, Jr. et al. . |
| 5,059,204 | 10/1991 | Lawson et al. . |
| 5,155,509 | 10/1992 | Kleinberg . |
| 5,268,196 | 12/1993 | Boulos et al. . |
| 5,658,306 | 8/1997 | Kieturakis et al. ........... 606/184 |
| 5,683,415 | 11/1997 | Brunken .................... 606/222 |

OTHER PUBLICATIONS

Marking Methods, Inc., "Electro–Chemical Marking?," (Copyright Oct. 21, 1975) Revised Printing 1992.

*Primary Examiner*—Michael Buiz
*Assistant Examiner*—Julian W. Woo
*Attorney, Agent, or Firm*—Baker & Daniels

[57] ABSTRACT

A medical device for surgical procedures is provided which includes an instrument having a working end defined by a portion of the instrument that can be visualized in a surgical field during a micro-invasive or minimally invasive surgical procedure. The working end includes a tissue manipulating element and a non-reflective outer surface, which covers the working end in its entirety so that the outer surface is free from glare points. The outer surface of the working end is preferably electrochemically etched to form a darkened metal oxide composition surface. The invention also includes micro-invasive surgical assemblies, which include a light source for illuminating the surgical field and visualization means as well as an instrument with a non-reflective working end. Processes for providing a surgical article with a non-reflective surface are also provided. The processes include placing an electrode adjacent the working end of the article and maintaining a gap between the article and the electrode. Electrolyte is supplied to the gap while passing an electric current between the article and electrode to provide a substantially uniform non-reflective surface to the entire working end of the article.

13 Claims, 8 Drawing Sheets

NON-REFLECTIVE SURFACES FOR SURGICAL PROCEDURES

FIELD OF THE INVENTION

The present invention relates to devices particularly suited for micro-invasive and minimally invasive surgeries and methods for making the devices. Specifically, the invention concerns surgical tools having antireflective surfaces that do not interfere with visualization of the surgical site.

BACKGROUND OF THE INVENTION

In recent years, there has been a trend towards developing less invasive surgical methods, which avoid the trauma and expense of traditional surgical approaches. In minimally invasive surgical techniques, the site of pathology is accessed through portals rather than through a significant incision thus preserving the integrity of intervening tissues. In some cases, these minimally invasive techniques require only local anesthesia, reducing post-operative recovery time and the risk of complications. Many percutaneous procedures have also been developed. The surgical site is accessed through a cannula and visualized either directly, with an endoscope inserted into a cannula or with other visualization means such as fluoroscopic X-ray.

Many developments have also been made in intricate and micro-surgical fields such as surgical ophthalmology and neurosurgery where extreme precision is essential. In these fields, surgical cutting probes are used to separate and remove pathologies from delicate structures. Fine discrimination is required to avoid damaging healthy tissue. Discrimination at this level requires bright lighting and specialized tools.

These new surgical procedures all share common needs: visualization means, a light source and specialized tools. Surgical instruments have been modified in size, shape and character to accommodate the smaller surgical fields. Various visualization and illumination means, such as surgical microscopes and fiber optic microscopes, are commercially available in the field. These advances in surgical tools and procedures have led to a new problem. Surgical instruments typically have a highly reflective surface that causes a glare in the surgical field under the conditions of minimally invasive procedures or micro-surgeries. This glare interferes with proper visualization of the instrument and the surgical field. This is particularly a problem when working with extremely small and delicate structures where even a fraction of a millimeter can be the difference between success and failure.

The glare caused by the reflective surface of ophthalmic microsurgical tools may also aggravate a condition known as light induced retinal damage. Exposure to the intense light of an operating microscope illumination system can cause light induced retinal damage. The onset and severity of light induced retinal damage is thought to be affected by the intensity of light per unit area of retina exposed, the duration of exposure and the wavelength of the light source. Because during eye surgery, it is frequently necessary to directly illuminate the eye with a strong illumination source, eye surgery patients are susceptible to light induced retinal damage. The glare of surgical tools may aggravate this condition by reflecting light and increasing the intensity of the light thereby exposing sensitive eye structures to damaging light. The glare interfering with the surgeon's visualization of the eye structures may also lengthen the duration of the surgery and therefore the duration of exposure to light.

Therefore, a need has remained for surgical instruments that do not interfere with visualization of the microsurgical site. These instruments must address the problem of glare without noticeably increasing the friction characteristics or compromising the durability and strength of the instrument. Furthermore, the instruments must be cost-effective because many of the devices are disposable to eliminate disease transmission risks.

Although there are many known methods for providing surface markings to metal articles, none of these have satisfied this new need for non-glare surgical instruments. Surface treatments can be enveloping or selective. One enveloping method is ebonizing or black oxide surface treatments, which have been used to create black chrome. In such procedures, the article is immersed in acid to etch the surface and then boiled in a caustic black salt bath at high temperatures for about one hour. These methods are harsh and costly for surgical instruments. Laser and electrochemical processes have been used for selective marking of surgical instruments. Lasers have been used to burn the surface of an article to create bands for depth markings and alphanumerics. Electrochemical processes have also been used to create markings on metal articles through the use of stencils or masking. For example, U.S. Pat. No. 4,408,215 to Kitchen discloses selectively marking a surface by selectively firing electrodes through a stencil to mark the surface with alphanumeric characters.

None of these procedures have addressed the problem of surgical glare. Lasers are suited for only selective markings. Darkening a large area by laser dimensionally and structurally changes the article and the large-scale use of laser for darkening an article is impractical and costly. Furthermore, the selective markings currently applied to surgical instruments tend to distort the glare and worsen its effects.

Accordingly, a need has remained for cost-effective means for reducing surgical glare that does not corrupt the integrity of the instrument or increase friction.

SUMMARY OF THE INVENTION

Briefly describing one aspect of the invention, a medical device for surgical procedures is provided which includes an instrument having a working end defined by a portion of the instrument that can be visualized in a surgical field during a surgical procedure. The working end includes a tissue manipulating element and a non-reflective outer surface that covers the working end in its entirety so that the outer surface is free from glare points. The outer surface of the working end is preferably electrochemically etched to form a darkened metal oxide composition surface. The invention also includes surgical assemblies that include a light source for illuminating the surgical field and visualization means as well as an instrument with a non-reflective working end.

The invention also provides processes for providing a surgical article with a non-reflective surface. The processes include placing an electrode adjacent the working end of the article and maintaining a gap between the article and the electrode. Electrolyte is supplied to the gap while passing an electric current between the article and electrode to provide a substantially uniform non-reflective surface to the entire working end of the article. In another embodiment, the process includes providing an electrochemical treatment vessel containing non-reflective etching solution. The working end of the article is immersed into the etching solution as an electric current is passed between the electrode and the article. In some embodiments, the article is rotated as the current is applied to ensure that the entire outer surface of the working end of the article is treated.

Accordingly, it is one object of the invention to provide improved surgical instruments for minimally invasive and delicate surgical procedures. One benefit of the invention is that it provides instruments that reduce glare for virtually any surgical procedure. Another benefit of this invention is that it aids in increasing the availability and success of minimally invasive and delicate surgical procedures. These and other objects, advantages and features are accomplished according to the devices and methods of the present invention.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

The present invention provides surgical instruments that facilitate visualization of at surgical field. The instruments have a surface that is nonreflecting and capable of absorbing light. The antireflective surface is particularly useful in any percutaneous and micro-surgical setting or any other surgical setting that requires micro-precise manipulations accompanied by appropriate visualization of the field. The invention also provides methods for making the instruments.

Figure 1:
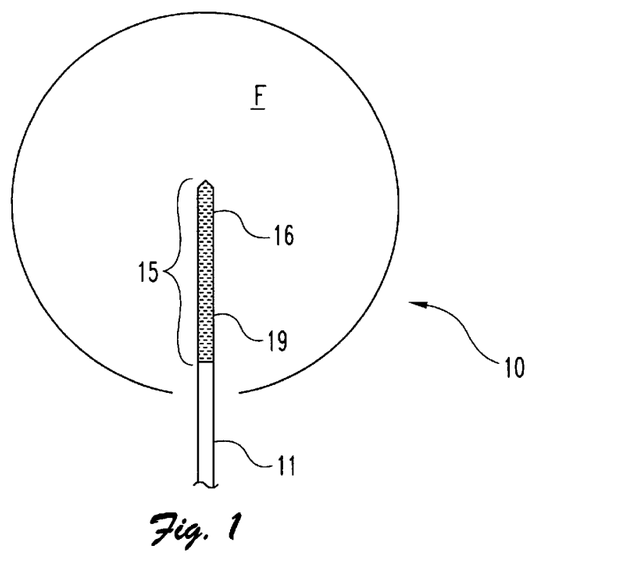
FIG. 1 is a side perspective view of the working end of a surgical instrument within a surgical field.
Figure 2:
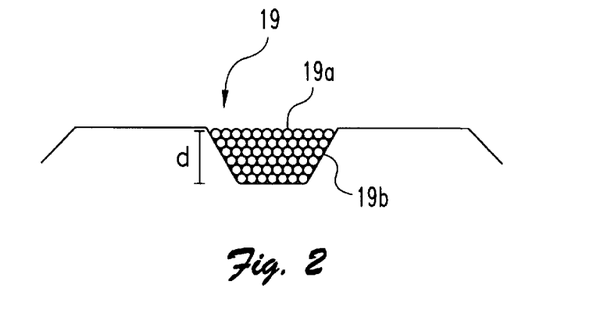
FIG. 2 is an enlarged view of the non-reflective surface of the working end of the instrument of FIG. 1.
Figure 3:
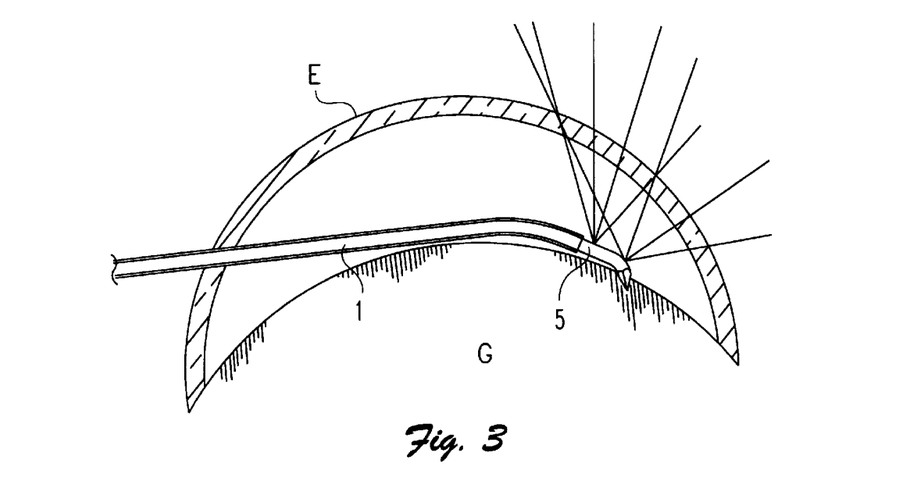
FIG. 3 is an illustration of an ophthalmic surgical tool inserted into an eye and showing glare points.

A medical device for surgical procedures in accordance with a preferred embodiment of the invention is depicted in FIGS. 1–2. The device 10 includes an instrument 11 having a working end 15 defined by a portion of the instrument 11 which can be visualized in a surgical field F during a surgical procedure. The working end 15 has a tissue manipulating element 16 and a non-reflective outer surface 19. The outer surface 19 covers the working end 15 in its entirety so that the working end 15 is free from glare points. Referring FIG. 3, the term glare points G is used herein to refer to locations on the working end 5 an article or instrument 1 which visibly reflect light where viewed in a surgical field F, particularly when a microsurgical or endoscopic light source, is used. Glare points G reflect to such an extent that they may interfere with the surgeon's visualization of the surgical site.

Reduction of glare is accomplished according to the present invention by providing the surface of the instrument with an antireflective surface. The antireflective surface is preferably provided using an electrochemical reaction.

One advantage of electrochemically treating instruments to provide a non-reflective surface is that the process is easily controlled and does not adversely affect the surgical instrument. The process can be controlled with respect to the composition of the electrolyte, temperature, electric current density and time. The particular electrolytic process is not important so long as the article is provided with an antireflective surface that does not substantially increase the friction properties of the article.

According to a preferred embodiment of the invention, the working end of the article is contacted with an electrolyte near an electrode and subjected to a low voltage, low ampere alternating current. Under the influence of the electrolyte and an alternating current, the surface is etched to form etch depressions 19a of a particular depth d and then a metal oxide composition 19b is deposited in each etch depression 19a to darken the surface 19. The depth d of the etch is thought to be dependent upon several factors including the voltage and gap between the electrode and the instrument, length of exposure time, electrolyte composition and temperature. Preferably, the depth d of the etch and the metal oxide composition layer is between about 0.0001 and about 0.010 inches deep. Most preferably, the depth d of the etch is in the light etch range, about 0.0001 to about 0.001 inches deep. Surgical instruments are preferably etched so that the roughness of the etch depressions 19a are imperceptible to a human touch and invisible at 20–30× magnification.

Figure 4:
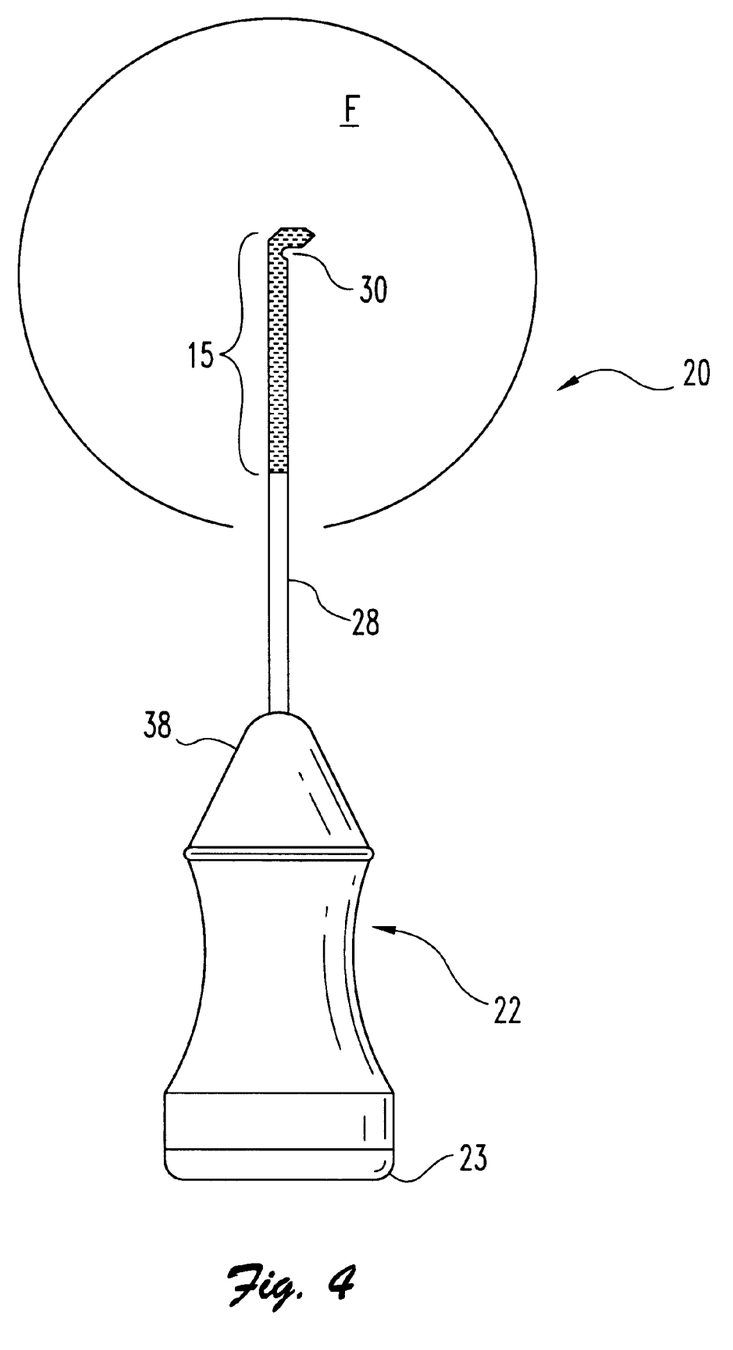
FIG. 4 is a side perspective view of a surgical instrument according to the present invention.

The non-reflective surfaces of this invention can be applied to virtually any metallic surgical instrument that may be used with a light source. For example, the instrument may be a surgical cutter such as is used in ophthalmic procedures. One such instrument, depicted in FIG. 4, is a vitrectomy probe disclosed in U.S. Pat. No. 5,047,008 to de Juan, Jr., et al. and assigned to Storz Instrument Company. The probe 20 includes a housing 22 having, a fitting end 23 which includes vacuum and fluid inlet fittings (not shown) and a nose end 38. The probe 20 supports a probe needle 28 in the rose section 38 of the housing 22. The probe needle 28 defines a port or tissue cutting opening 30. An inner tubular member (not shown) with a cutting blade reciprocates within the probe needle 28. In some embodiments, the distal portion of the inner tubular member and cutting blade may also be provided with a non-reflective surface. According to the '008 Patent, the probe needle is preferably T304 stainless steel because it has a sufficiently smooth interior bore. Fortunately, the present invention allows the use of this alloy for its smoothness without the glare typically suffered with stainless steel.

Figure 5:
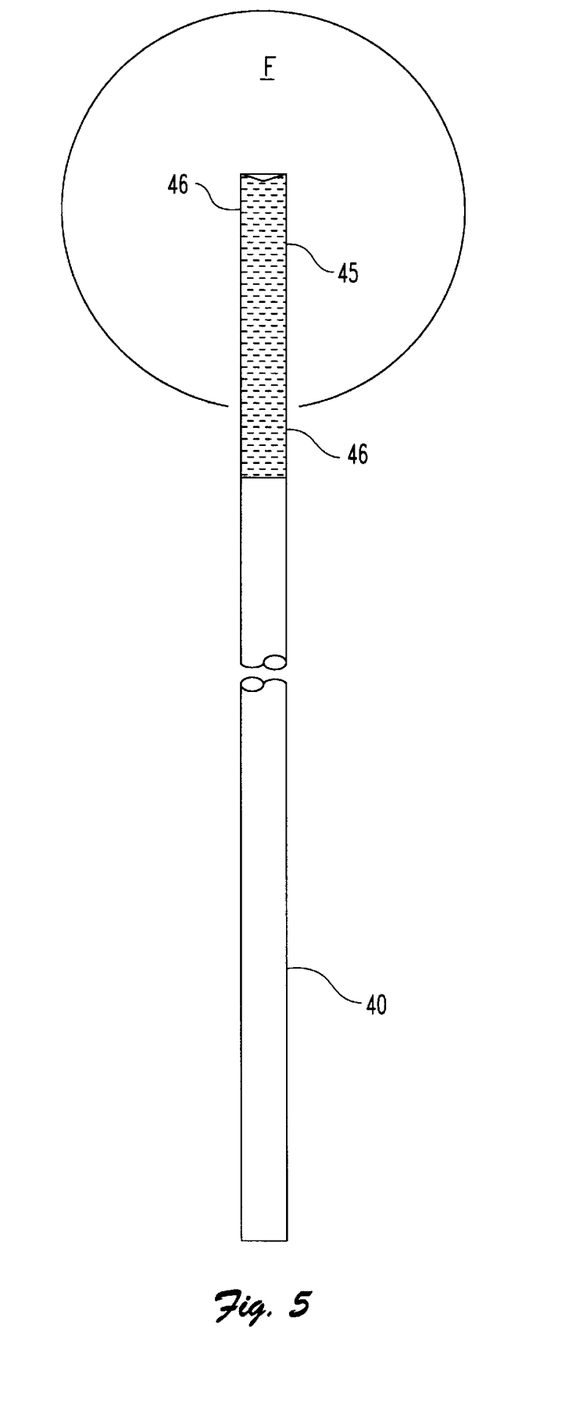
FIG. 5 is a side elevational view of a surgical instrument.

It is understood that the particular size and configuration of the instrument will depend on the particular surgical application. For example, many improvements have been made to surgical cutters. The invention contemplates virtually any surgical instrument with a working end having the non-reflective working surfaces described herein. For example, the surgical instrument may be any elongated surgical article, including cannulas and retractors such as are used in endoscopic surgery. As shown in FIG. 5, a cannula 40 for percutaneous access to tissues deep within a patient's body includes a working end 45 having a tissue-manipulating element 46. The element 46 serves as a tissue retraction surface in that it retracts tissue to maintain a channel through the tissue to the surgical field F. The entire working end 45 is provided with a non-reflective surface 49 according to this invention. Although a specific cutter and cannula are described here as examples, the invention includes any surgical instrument with a working end having the non-reflective surfaces of this invention. Advantageously, the methods of this invention can be applied to standard surgical instruments and to other instruments that may be later invented to provide an antireflective surface to the working ends of the instruments.

In other embodiments, the invention includes a micro-invasive surgical assembly, including a light source for illuminating a surgical field and visualization means for visualizing the surgical field in addition to the instrument having a non-reflective surface. Any suitable visualization and illumination means is contemplated, including devices, which are now known or may become known later in the art.

Figure 6:
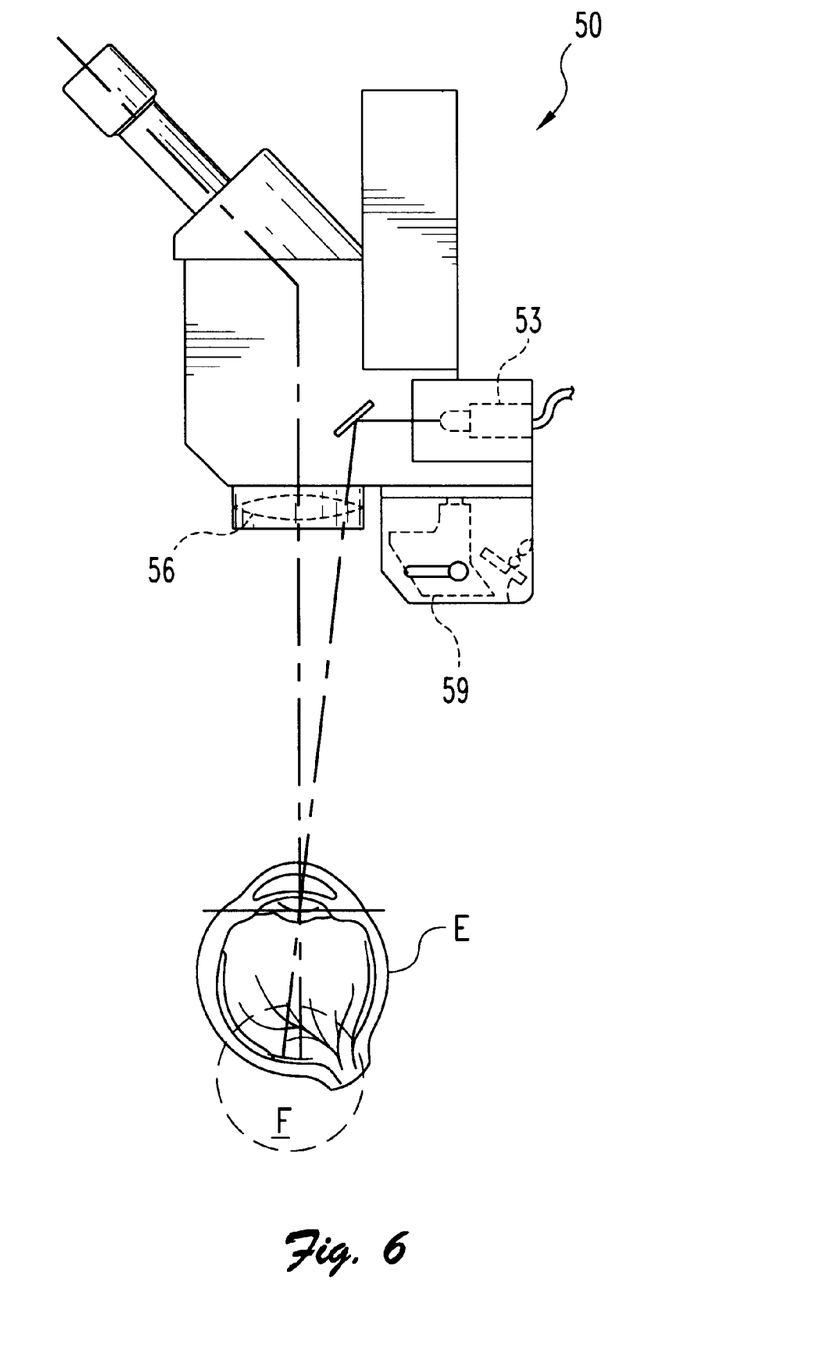
FIG. 6 is a side view of a binocular microscope shown relative to a schematic illustration of the eye.

In some embodiments, the visualization means and light source includes a surgical microscope as known in the art. Such microscopes are used by surgeons to visualize delicate structures and the positioning and functioning of instruments during micro-surgical procedures. One such microscope is disclosed in U.S. Pat. No. 5,155,509 to Kleinberg and assigned to Storz Instrument Company. FIG. 6 shows a binocular microscope 50 positioned above a surgical site in the eye E as disclosed in the '509 Patent. A light source 53 is positioned to illuminate the surgical field F within the eye E. The scope of the '509 Patent also includes an oblique illumination apparatus 59 affixed to the underside of the microscope 50 adjacent the microscope objective lens 56.

Figure 7:
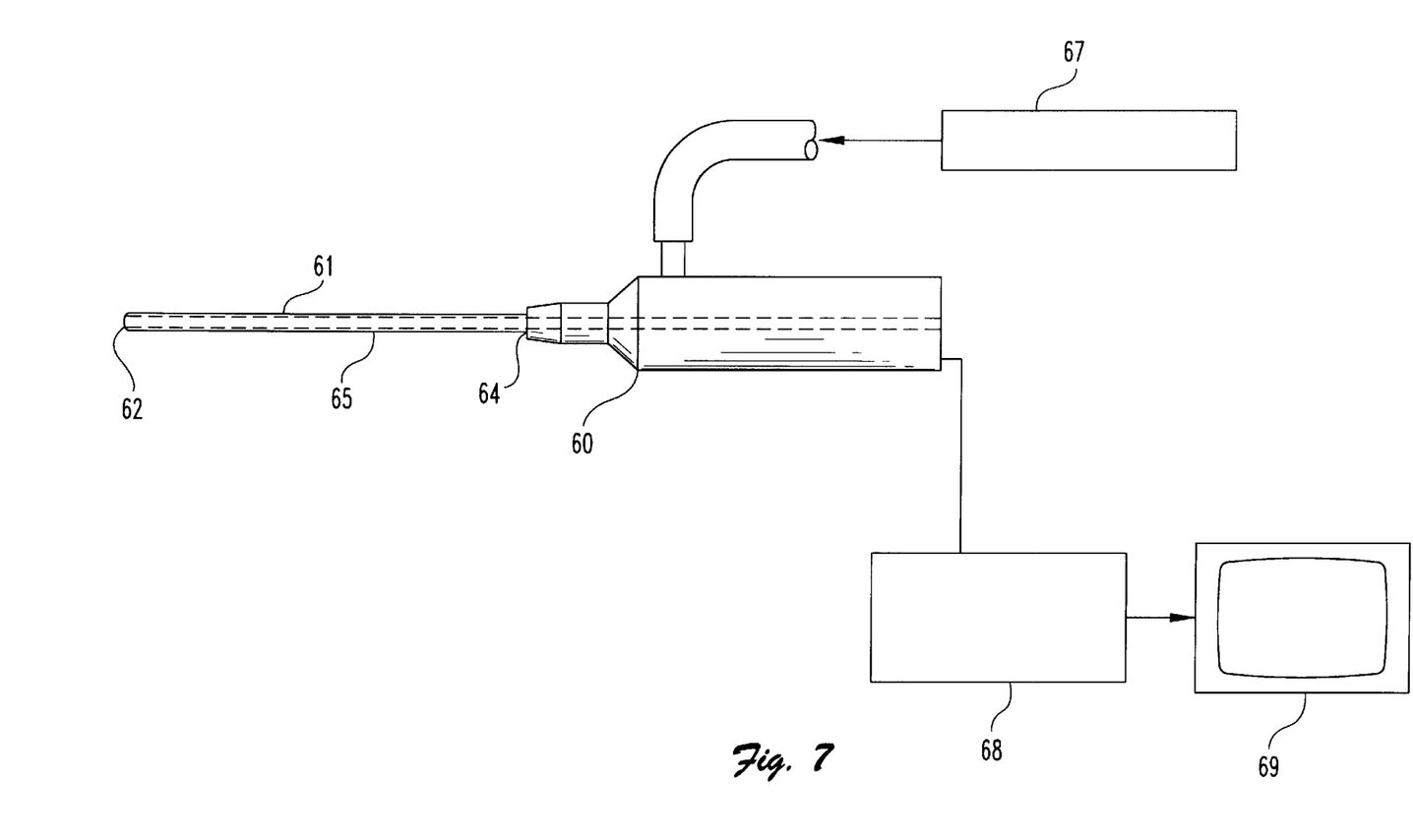
FIG. 7 is a side elevational view of an endoscope assembly.

The micro-invasive surgical assemblies of this invention may also include an endoscope. FIG. 7 depicts a typical endoscope assembly. The endoscope 60 includes an elongated cannula 61 having an outer diameter sized for percutaneous introduction through skin and tissue of a patient to a surgical site within the patient's body. The cannula 61 includes a distal working end 62 and an opposite proximal end 64. In some embodiments, at least one channel 65 is defined through the cannula 61 extending between the two ends 62, 64. Channels may be used for visualization or for passage for percutaneous instruments. The endoscope 60 of FIG. 7 includes a viewing element. The viewing element has a first end connectable to a viewing apparatus, such as an eyepiece or camera, and a second end positionable adjacent the distal working end of the cannula. In one embodiment, the viewing element includes a fiber optic scope and a lens at the second end. In one specific embodiment depicted in FIG. 7, the endoscope includes a light source 67 that conducts light to the surgical site. In some embodiments, a probe containing light conductive fibers is provided as is known in the art. The image is then conducted from the site to a video camera 68. The camera 68 produces a continual view of the surgical site on video monitor 69, which the surgeon views while manipulating surgical instruments within the surgical site.

Although a specific endoscope assembly is depicted in FIG. 7, the invention is not so limited. The invention contemplates any visualization means and light source assemblies. Both rigid and bendable endoscopes are contemplated. In some cases, the surgical site is accessed through a working channel in the endoscope. In other cases, the surgical site is accessed from a different portal through skin and tissue and light and visualization is provided with an endoscopic probe. In either case, light reflecting from the working end of the surgical instrument can cause glare and inhibit or obstruct the surgeon's view of the field unless the working end is provided with the non-reflective surfaces of this invention.

The invention also includes methods and processes for providing a surgical article with a non-reflective surface. The processes generally include placing an electrode adjacent the working end of the article and maintaining a gap between the article and the electrode. Electrolyte is supplied to the gap while an electric current is passed between the article and electrode to provide a substantially uniform non-reflective surface to the entire working end of the article. This invention exploits the electrochemical reaction that occurs under these conditions to etch and darken the surface without compromising the strength, durability or smoothness of the instrument.

Figure 8:
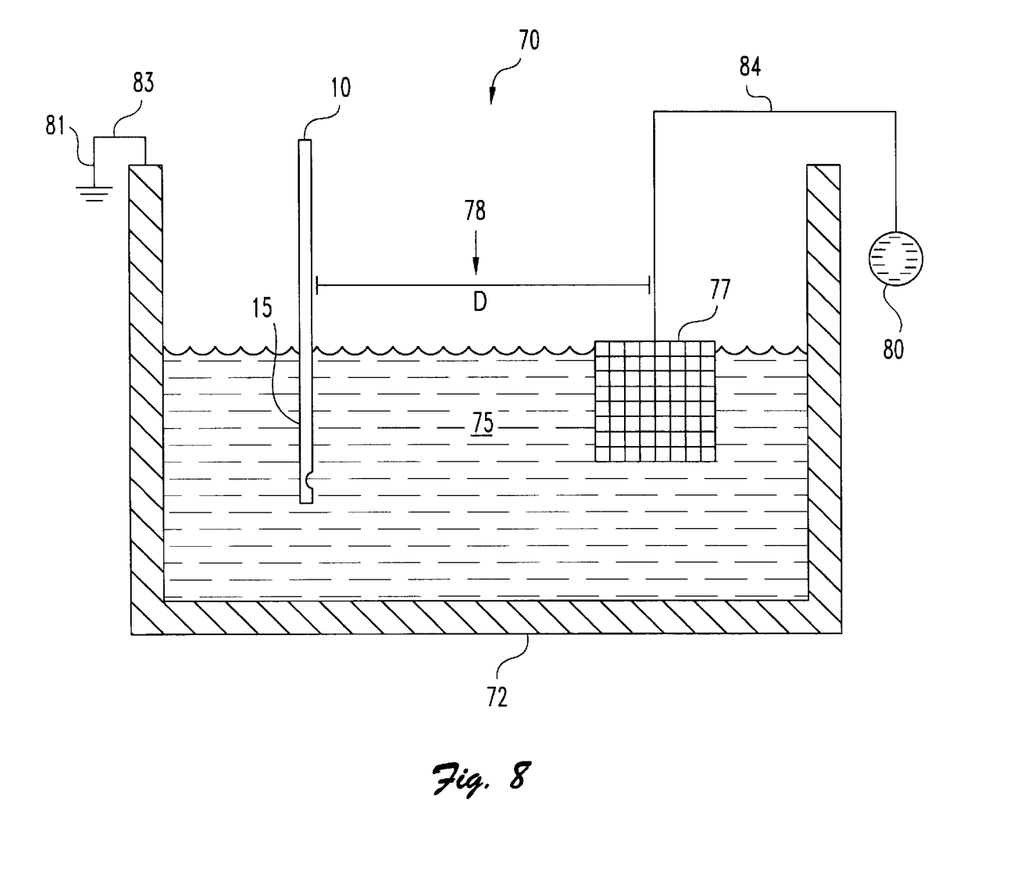
FIG. 8 is a surgical instrument-non-reflective surface applicator assembly.
Figure 9:
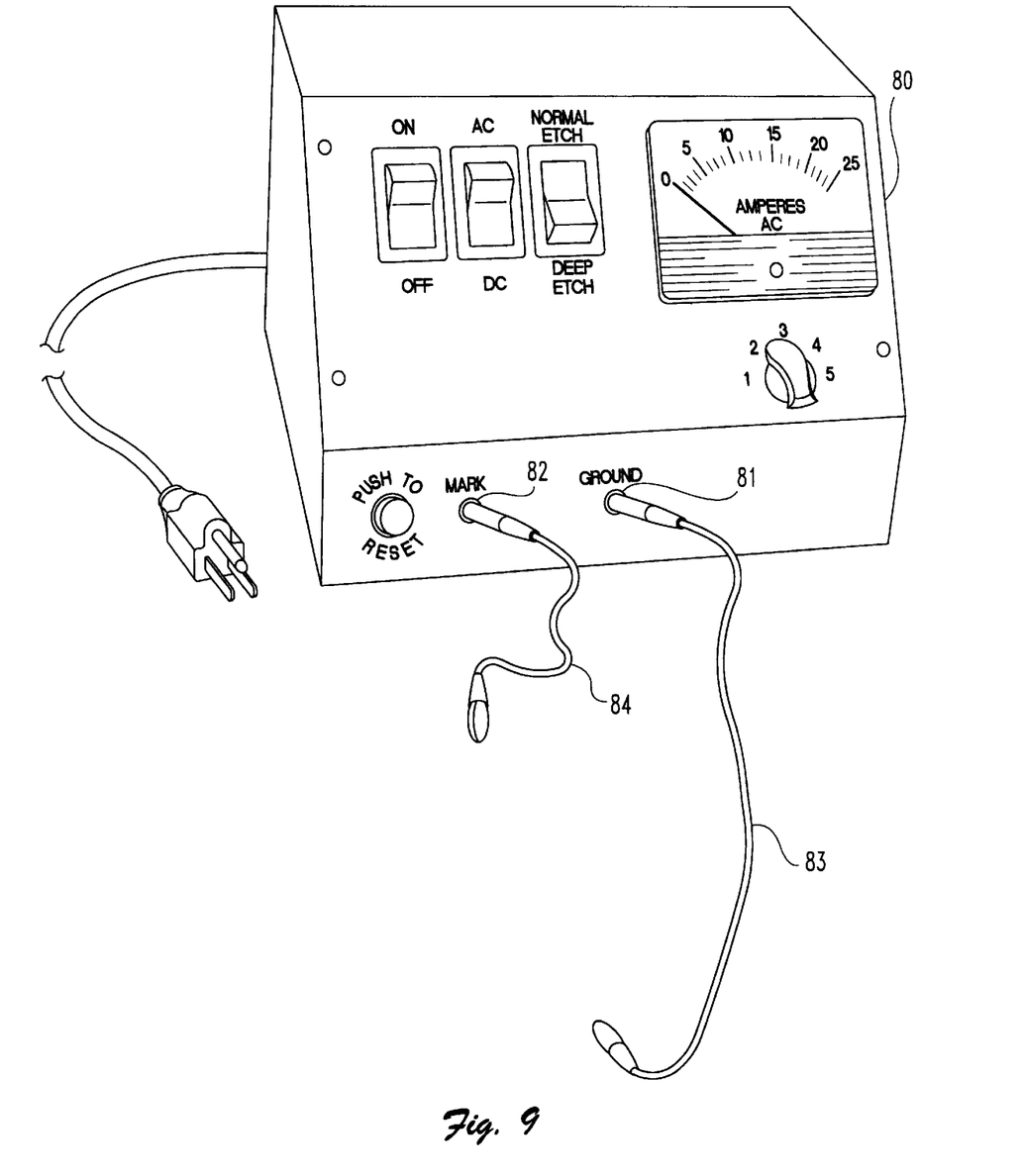
FIG. 9 is a power unit for a non-reflective surface applicator assembly.

A non-reflective surface applicator assembly 70 according to a preferred embodiment of this invention is shown in FIG. 8. The assembly 70 includes an electrochemical treatment vessel 72 containing a non-reflective etching solution 75. The vessel can be any suitable container that is made of a material resistant to electrolytic action. The assembly includes an electrode 77 immersed in the solution 75 and means are provided for connecting the electrode to an electrical power source 80. The electric current can vary but is generally several amperes to several 10 amperes/cm$^2$. In one embodiment, a power source 80 such as depicted in FIG. 9 is used. A similar device is available from Marking Methods, Inc. The device 80 includes ports 81, 82 for ground and marking wires, 83, 84. The device 80 provides an alternating current through wire 84. Wire 84 connects electrode 77 electrically to the power source 80. Wire 83 grounds the vessel 72.

According to the invention, the working end 15 of the instrument 10 to be treated is placed into the solution 75 while maintaining a gap 78 between the electrode 77 and the working end 15. An alternating electric current is passed from the power source 80 through the electrode 77 and the etching solution 75 to the working end 15. In this way, a non-reflective surface is applied to the entire working end 15 of the article 10 so that the working end 15 is free from glare points. In some embodiments the instrument is rotated within the etch solution to ensure a uniform surface. However, this is not generally necessary when the assembly 70 is employed. This provides a permanent antireflective surface without distorting or deforming the instrument.

The electrolyte and operating conditions are selected based upon the material of the work piece and the desired depth of the etch. The particular electrode and electrolyte is not critical. Preferably the electrode will be an excellent conductor which is impervious to liquids and will not break down electrically or mechanically or chemically. Typical electrode materials include carbon, stainless steel, copper, aluminum and combinations thereof In one embodiment, a carbon electrode is selected because carbon is an excellent conductor and it does not corrode or otherwise break down electrically or mechanically when exposed to solvents and chemicals.

The electrolyte fluid acts as a conducting medium for the etching current and provides metallic salts for forming oxides. The particular electrolyte composition depends upon the material of the article. For iron based materials, such as stainless steel, the electrolyte solution may be a sodium nitrate solution. The electrolyte solution will generally be pH balanced buffered salt solutions that will not harm the articles. Typical electrolytes include sulfuric acid, sodium sulfate, nitric acid, carbonates and chlorates of the alkali metals. Preferably, the electrolyte is MSC-1. However, the particular electrolyte solution is not critical and appropriate solutions are commercially available. Preferred solutions such as MSC-1 are available from Marking Methods, Inc., Mentor, Ohio.

The gap 78 between electrode 77 and the instrument 10 is also not critical so long as both the working end 15 of the instrument 10 and the electrode 77 are submersed in electrolyte 75. Gap 78 may have a distance D that is between about 0.04 inches and about 12 inches, preferably distance D is no more than about 5 inches and at least about 0.4 inches for technical ease.

Figure 10:
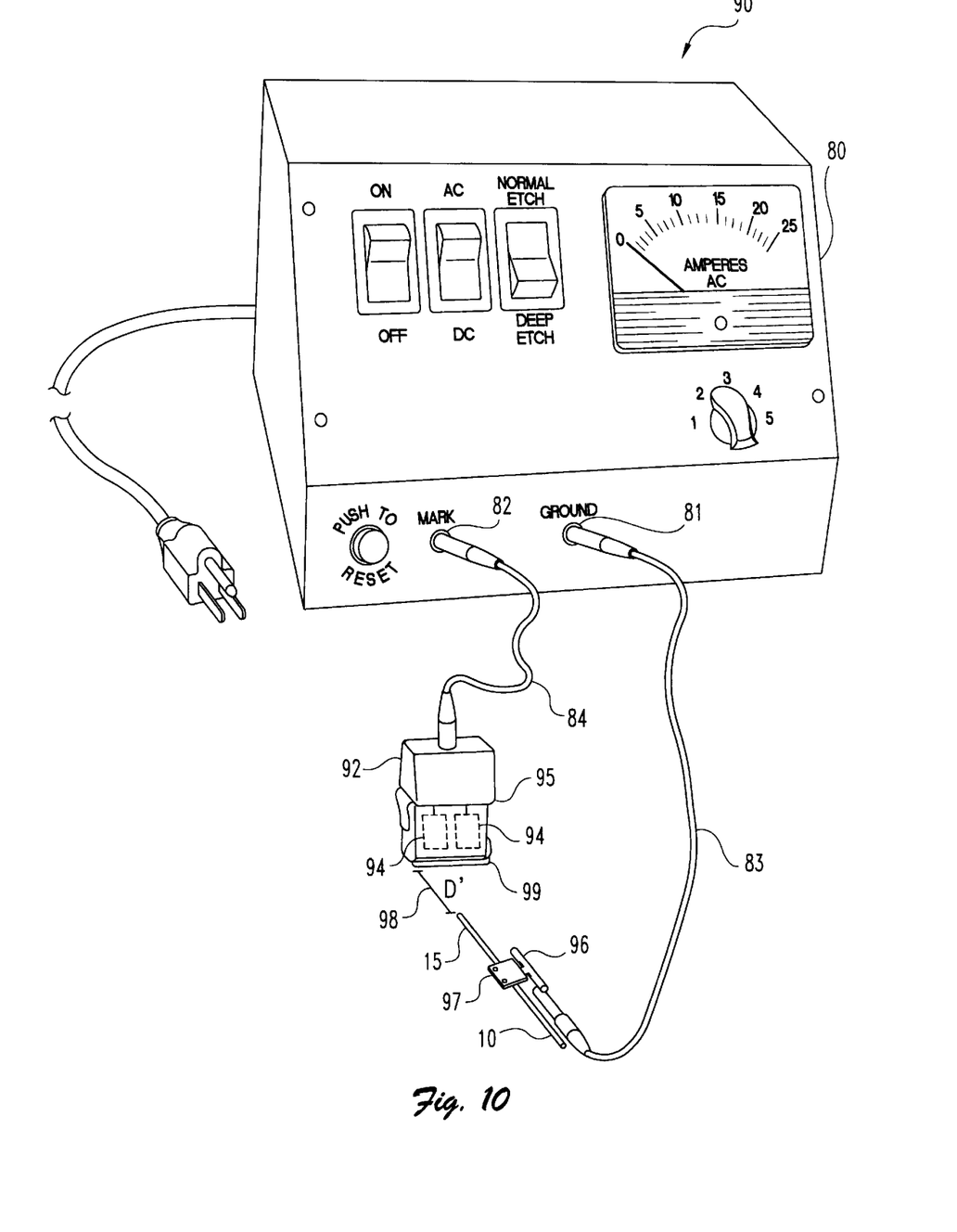
FIG. 10 is a surgical instrument-non-reflective surface applicator assembly.

In another embodiment, a process employs the assembly 90 depicted in FIG. 10. The assembly includes the power source 80 shown in FIG. 9. A marking applicator 92 is electrically connected to wire 84. The marking head 95 of the marking applicator 92 includes electrodes 94, which are electrically connected to the power supply 80. The instrument 10 to be treated is supported by clip 97 which is connected to ground wire 83. The process includes placing the marking head 92 adjacent the working end 15 of the instrument 10 while maintaining a gap 98. The gap distance D' is not critical to the invention and will be determined by the requirements of the particular marking applicator 92. Non-reflective surface solution is supplied to the gap 98 in contact with both the working end 15 and the electrodes 94. Preferably, the marking applicator includes means 99 for supplying solution to the gap 98. The particular means is not critical and various means for supplying solution in an electrolytic marking device are known and commercially available. An alternating current is passed from the power supply 80 to the electrodes 94 in the marking applicator 92. In this embodiment, the instrument to be marked is rotated relative to the marking head 95 to ensure that the entire working end 15 has a uniform non-reflective surface. The instrument 10 may be rotated manually or the assembly may be provided with rotating means 96 for rotating the instrument 10.

The devices of this invention can also be provided with informational markings such as various complex patterns or alpha-numerics. The informational markings will be provided using methods known in the art. If the methods include electrochemical etching, the oxide layer of the markings will be of a different thickness than the thickness of the oxide layer of the non-reflective surface. The devices can be provided with depth markings that are darkened bands at a particular interval over a length of the device including the non-reflective surface. The depth markings are created as are known in the art. Alpha-numerics can be provided above or over the non-reflective surface using methods known in the art. Such markings are created by masking portions of the device or with a stencil. Various electrochemical marking products are known in the art and are commercially available from Genesis One (Lombard, Ill.) and others.

The present invention shall be more concretely explained with the following examples, which are considered to be merely representative of the present invention and thus should not be considered as limiting.

EXAMPLE 1

The distal end of an outer cannula of a stainless steel surgical cutter was electrochemically treated in an electrochemical vessel to provide the surface of the distal end with an antireflective surface. The vessel contained a carbon electrode immersed in MSC-1 electrolyte salt solution from Marking Methods (Mentor, Ohio). The distal end of the cutter was placed in the electrolyte solution. A gap of about five (5) inches was maintained between the cutter and the electrode. The cutter was grounded by connecting to a grounding wire and functioned as the anode in the electrochemical reaction. Alternating current of low voltage was fed through the electrode (cathode) for about three seconds. The alternating current first etched the surface and then re-deposited a combination of the metal oxide and electrolyte salts to produce an antireflective darker etched surface. After the electrolytic treatment, the surface of the cutter was ultrasonically cleaned as known in the art. The surface of the distal end of the cutter was uniformly and permanently darkened to remove all glare points without weakening or deforming the cutter. The darkened surface of the cutter was smooth to the touch and did not perceptively increase the friction characteristics of the cutter.

EXAMPLE 2

The distal end of a stainless steel endosurgical probe is electrochemically treated in an electrochemical vessel to provide the surface of the distal end with an antireflective surface. The vessel contains a stainless steel electrode immersed in MSC-1 electrolyte salt solution from Marking Methods (Mentor, Ohio). The distal end of the probe is placed in the electrolyte solution while maintaining a gap between the electrode and the distal end. The probe functions as the anode. Alternating current of low voltage is fed through the electrode (cathode) for a few seconds as the probe is rotated within the solution. The alternating current first etches the surface and then re-deposits a combination of the metal oxide and electrolyte salts to produce an antireflective darker etched surface. After the electrolytic treatment, the surface of the probe is cleaned to remove residual electrolyte by vigorously wiping the distal end of the probe with a solution of APC Cleaner (Marking Methods, Mentor, Ohio). The surface of the distal end of the probe is uniformly and permanently darkened to remove all glare points without weakening or deforming the probe. The darkened surface of the probe is smooth to the touch and does not increase the friction characteristics of the cutter.

EXAMPLE 3

A non-reflective surface was applied to one portion of a stainless steel sample using a non-reflective surface applicator assembly as described in Example 1. The surface of the distal end of the sample was uniformly and permanently darkened without weakening or deforming the sample. The darkened surface of the cutter was smooth to the touch and did not perceptively increase the friction characteristics of the sample. The sample was placed under a light source and glare points were observed on the proximal (untreated) end of the sample. The distal end of the sample did not exhibit any glare points.

EXAMPLE 4

A non-reflective surface is applied to the working end of a surgical assembly using the assembly depicted in FIG. 10. The instrument is supported by a clip and the marking head is placed adjacent the working end of the instrument. A gap of about 1 mm is maintained. An alternating current is passed from the power supply to the electrodes in the marking applicator while the instrument is rotated relative to the marking head to ensure that the entire working end has a uniform non-reflective surface.

The present invention economically and conveniently provides surgical articles with an antireflective surface using a safe and clean process. Surgical instruments having the non-reflective surfaces of this invention are not compromised as to strength, durability or friction properties. Instruments of this invention provide an advance in the fields of endoscopic and microsurgery because they eliminate the glare that is currently suffered in such surgeries.

While the invention has been illustrated and described in detail in the drawings and foregoing description, the same is to be considered as illustrative and not restrictive in character. It should be understood that only the preferred embodiments have been shown and described and that all changes and modifications that come within the spirit of the invention are desired to be protected.

What is claimed:

1. A medical device for surgical procedures, comprising:

an instrument having a working end defined by a portion of the instrument that can be visualized in a surgical field during a surgical procedure, said working end having a tissue manipulating element and said working end having an electrolytically etched non-reflective outer surface covering said working end in its entirety, said outer surface free from glare points.

2. The device of claim 1 wherein said non-reflective outer surface includes a metal oxide composition, said composition having a depth of about 0.0001 inches.

3. The device of claim 1 wherein said outer surface is etched to form etch depressions.

4. The device of claim 3 further comprising a darkened metal oxide composition deposited in said etch depressions.

5. The device of claim 4 wherein said etch depressions are between about 0.00005 inches to about 0.001 inches deep.

6. The device of claim 5 wherein said etch depressions are about 0.0001 inches deep.

7. The device of claim 1 wherein said instrument is a tissue cutter and said tissue manipulating element includes a tissue cutting opening.

8. The device of claim 1 wherein said instrument is an elongated surgical article arid said tissue manipulating element is a tissue retraction surface.

9. The device of claim 1 wherein said instrument is a cannula for accessing the surgical field.

10. A surgical assembly, comprising:

a light source for illuminating a surgical field;

visualization means for visualizing the surgical field; and an instrument having a working end defined by a portion of the instrument that can be visualized in the surgical field during a surgical procedure, said working end having a tissue manipulating element and said working end having an electrolytically etched non-reflective outer surface covering said working end in its entirety, said outer surface free from glare points.

11. The assembly of claim 10 wherein said light source is a probe containing light conductive fibers.

12. The assembly of claim 11 wherein said visualization means includes a video camera and monitor.

13. The assembly of claim 10 wherein said visualization means includes a surgical microscope.

* * * * *